(12) United States Patent
DeFossa et al.

(10) Patent No.: US 7,781,459 B2
(45) Date of Patent: Aug. 24, 2010

(54) CARBOXYALKOXY-SUBSTITUTED ACYL-CARBOXYPHENYLUREA DERIVATIVES AND THEIR USE AS MEDICAMENTS

(75) Inventors: Elisabeth DeFossa, Idstein (DE); Dieter Kadereit, Kelkheim (DE); Thomas Klabunde, Kelkheim (DE); Hans-Joerg Burger, Morristown, NJ (US); Andreas Herling, Frankfurt (DE); Karl-Ulrich Wendt, Frankfurt (DE); Erich Von Roedern, Hattersheim (DE); Karl Schoenafinger, Alzenau (DE); Alfons Enhsen, Buettleborn (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 39 days.

(21) Appl. No.: 11/613,433

(22) Filed: Dec. 20, 2006

(65) Prior Publication Data

US 2007/0088083 A1 Apr. 19, 2007

Related U.S. Application Data

(63) Continuation of application No. 10/679,550, filed on Oct. 6, 2003, now abandoned.

(60) Provisional application No. 60/444,890, filed on Feb. 4, 2003.

(30) Foreign Application Priority Data

Oct. 4, 2002 (DE) .................................. 102 46 434

(51) Int. Cl.
*A61K 31/445* (2006.01)
*C07D 211/08* (2006.01)

(52) U.S. Cl. ........................ 514/331; 546/237; 546/247; 514/461; 514/532; 514/571; 514/594; 562/512; 562/579

(58) Field of Classification Search ................. 514/331, 514/461, 532, 571, 594; 546/237, 247; 562/512, 562/579
See application file for complete search history.

(56) References Cited

U.S. PATENT DOCUMENTS

| 6,221,633 B1 | 4/2001 | Ertl |
| 6,221,897 B1 | 4/2001 | Frick et al. |
| 6,245,744 B1 | 6/2001 | Frick et al. |
| 6,342,512 B1 | 1/2002 | Kirsch |
| 6,506,778 B2 * | 1/2003 | Defossa et al. ............... 514/331 |

FOREIGN PATENT DOCUMENTS

| DE | 694 05 815 | 2/1998 |
| DE | 10142734 | 3/2003 |
| EP | 0 193 249 | 9/1986 |
| EP | 0 462 884 | 12/1991 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/63208 | 10/2000 |
| WO | WO00/64876 | 11/2000 |
| WO | WO00/64888 | 11/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/83451 | 11/2001 |
| WO | WO 01/85695 | 11/2001 |
| WO | WO01/94300 | 12/2001 |

OTHER PUBLICATIONS

Asakawa A. et al., Cocaine-Amphetamine-Regulated Transcript Influences Energy Metabolism, Anxiety And Gastric Emptying In Mice, Horm Metab Res, (2001), vol. 33, pp. 554-558.

(Continued)

*Primary Examiner*—Ardin Marschel
*Assistant Examiner*—Zohreh Vakili
(74) *Attorney, Agent, or Firm*—Barbara E. Kurys

(57) ABSTRACT

The invention relates to acyl-carboxyphenylurea derivatives and to their physiologically tolerated salts and physiologically functional derivatives.

Compounds of the formula I,

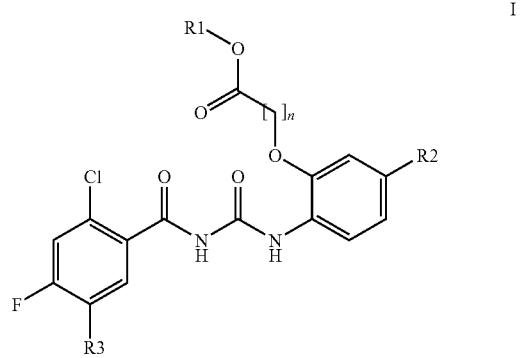

in which the radicals have the stated meanings, and the physiological tolerated salts thereof and processes for preparing them are described. The compounds are suitable for example for the treatment of type II diabetes.

8 Claims, No Drawings

OTHER PUBLICATIONS

Lee Daniel W. et al., Leptin Agonists As A Potential Approach To The Treatment Of Obesity, Drugs Of The Future, (2001), vol. 25, No. 9, pp. 873-881.

Okada Hiroshi et al., Synthesis And Antitumor Activities Of Prodrugs Of Benzoylphnylureas, Chem. Pharm. Bull., (1994), vol. 42, No. 1, pp. 57-61.

Rousset Monique et al., Growth-Related Glycogen Levels Of Human Intestine Carcinoma Cell Lines Grown In Vitro And In Vivo In Nude Mice, JNCI, (1980), vol. 65, No. 5, pp. 885-889.

Salvador Javier et al., Perspectives In The Therapeutic Use Of Leptin, Expert Opin. Pharmacother., (2001), vol. 2, No. 10, pp. 1615-1622.

Skwarski L. et al., Glycogen Content In The Gastric Mucosa Of Partially Resected Stomach; A Possible Relationship With The Development Of Cancer, Cancer Letters, (1998), vol. 127, pp. 123-128.

Takahashi Shigeki et al., Estimation Of Glycogen Levels In Human Colorectal Cancer Tissue: Relationship With Cell Cycle And Tumor Outgrowth, J. Gastroenterol, (1999), vol. 34, pp. 474-480.

Treadway Judith L. et al., Glycogen Phosphorylase Inhibitors For Treatment Of Type 2 Diabetes Mellitus, Exp. Opin. Invest. Drugs, (2001), vol. 10, No. 3, pp. 439-454.

Tyle Praveen, Iontophoretic Devices For Drug Delivery, Pharmaceutical Research, (1986), vol. 3, No. 6, pp. 318-326.

Yano Kazuyuki et al., Evaluation Of Glycogen Level In Human Lung Carcinoma Tissues By An Infrared Spectroscopic Method, Cancer Letters, (1996), vol. 110, pp. 29-34.

Zunfit H. J. F. et al., Carob Pulp Preparation For Treatment Of Hypercholesterolemia, Advances In Therapy, (2001), vol. 18, No. 5, pp. 231-236.

* cited by examiner

CARBOXYALKOXY-SUBSTITUTED ACYL-CARBOXYPHENYLUREA DERIVATIVES AND THEIR USE AS MEDICAMENTS

DOMESTIC PRIORITY CLAIM

This application claims priority under 35 U.S.C. §119 of U.S. Provisional Application No. 60/444,890 filed on Feb. 4, 2003.

PRIORITY CLAIM

This application claims priority under 35 U.S.C. §119 of German Application No. 10246434.0-42 filed on Oct. 4, 2002.

The invention relates to acyl-carboxyphenylurea derivatives and to their physiologically tolerated salts and physiologically functional derivatives.

Acylphenylurea derivatives have already been described as antitumor or antidiabetic agents in the prior art (EP 0 193 249 and WO 01/94300).

The invention was based on the object of providing compounds which display a therapeutically utilizable blood glucose-lowering effect. In particular, it was an object to find novel compounds which, compared to the compounds described in WO 01/94300 show better blood glucose-lowering effect.

The invention therefore relates to compounds of the formula I,

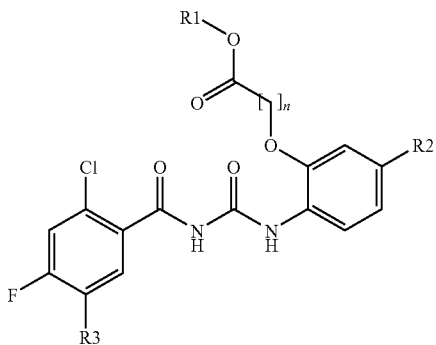

in which
R1 is H, $(C_1-C_6)$alkyl, $(C_0-C_6)$-alkyl-phenyl, wherein the phenyl ring is optionally mono- or disubstituted with F, Cl, Br, CN, OH, $(C_1-C_6)$-alkyl, O—$(C_1-C_6)$-alkyl, $CF_3$, $OCF_3$, COOH, COO$(C_1-C_6)$-alkyl or $CONH_2$;
R2 is H, $(C_1-C_6)$-alkyl, O—$(C_1-C_6)$-alkyl, CO—$(C_1-C_6)$-alkyl, COO—$(C_1-C_6)$-alkyl or $(C_0-C_6)$-alkylene-COOH;
R3 is H, F, Cl, Br, OH, $CF_3$, $NO_2$, CN, $OCF_3$, O—$(C_1-C_6)$-alkyl or $(C_1-C_6)$-alkyl; and
n is 1, 2, 3, 4, 5, 6, 7 or 8;

and pharmaceutically acceptable salts thereof.
Preference is given to compounds of the formula I in which
R1 is H or $(C_1-C_6)$-alkyl;
R2 is H, $(C_1-C_6)$-alkyl, O—$(C_1-C_6)$-alkyl, CO—$(C_1-C_6)$-alkyl, COO—$(C_1-C_6)$-alkyl or $(C_0-C_6)$-alkylene-COOH;
R3 is H, F, Cl, Br, OH, $CF_3$, $NO_2$, CN, $OCF_3$, O—$(C_1-C_6)$-alkyl or $(C_1-C_6)$-alkyl;
n is 1, 2, 3, 4, 5, 6, 7 or 8;

and pharmaceutically acceptable salts thereof.
Particularly preference is given to compounds of the formula I in which
R1 is H or $(C_1-C_6)$-alkyl;
R2 is H, COO—$(C_1-C_6)$-alkyl or —COOH;
R3 is H or F; and
n is 1, 2, 3 or 4;

and pharmaceutically acceptable salts thereof.
The invention relates to compounds of the formula I in the form of their racemates, racemic mixtures and pure enantiomers, and to their diastereomers and mixtures thereof.

The alkyl radicals in the substituents R1, R2 and R3 may be both straight-chain and branched.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

As used herein, the following definitions apply:
"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

"Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

"Oncosis" means a condition characterized by the formation of one or more neoplasms or tumors.

All references to "compound(s) of formula I" hereinafter refer to compound(s) of the formula I as described above, and their salts, solvates and physiologically functional derivatives as described herein.

The compound(s) of formula (I) may also be administered in combination with other active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, wafers, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are: all antidiabetics mentioned in the Rote Liste 2001, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin.

In another embodiment of the invention, the compounds of the formula I are administered in combination with a cholesterol absorption inhibitor such as, for example, ezetimibe, tiqueside, pamaqueside.

In another embodiment of the invention, the compounds of the formula I are administered in combination with a PPAR gamma agonist, such as, for example, rosiglitazone, pioglitazone, JTT-501, GI 262570.

In another embodiment of the invention, the compounds of the formula I are administered in combination with a PPAR alpha agonist, such as, for example, GW 9578, GW 7647.

In another embodiment of the invention, the compounds of the formula I are administered in combination with a mixed PPAR alpha/gamma agonist, such as, for example, GW 1536, AVE 8042, AVE 8134, AVE 0847, or as described in PCT/US00/11833, PCT/US00/11490, DE10142734.4.

In another embodiment of the invention, the compounds of the formula I are administered in combination with a fibrate such as, for example, fenofibrate, clofibrate, bezafibrate.

In another embodiment of the invention, the compounds of the formula I are administered in combination with an MTP inhibitor such as, for example, implitapide, BMS-201038, R-103757.

In another embodiment of the invention, the compounds of the formula I are administered in combination with a bile acid absorption inhibitor (see, for example, U.S. Pat. No. 6,245,744 or U.S. Pat. No. 6,221,897), such as, for example, HMR 1741.

In another embodiment of the invention, the compounds of the formula I are administered in combination with a CETP inhibitor, such as, for example, JTT-705.

In another embodiment of the invention, the compounds of the formula I are administered in combination with a polymeric bile acid adsorbent such as, for example, cholestyramine, colesevelam.

In another embodiment of the invention, the compounds of the formula I are administered in combination with an LDL receptor inducer (see U.S. Pat. No. 6,342,512), such as, for example, HMR1171, HMR1586.

In another embodiment of the invention, the compounds of the formula I are administered in combination with an ACAT inhibitor, such as, for example, avasimibe.

In another embodiment of the invention, the compounds of the formula I are administered in combination with an antioxidant, such as, for example, OPC-14117.

In another embodiment of the invention, the compounds of the formula I are administered in combination with a lipoprotein lipase inhibitor, such as, for example, NO-1886.

In another embodiment of the invention, the compounds of the formula I are administered in combination with an ATP-citrate lyase inhibitor, such as, for example, SB-204990.

In another embodiment of the invention, the compounds of the formula I are administered in combination with a squalene synthetase inhibitor, such as, for example, BMS-188494.

In another embodiment of the invention, the compounds of the formula I are administered in combination with a lipoprotein(a) antagonist, such as, for example, CI-1027 or nicotinic acid.

In another embodiment of the invention, the compounds of the formula I are administered in combination with a lipase inhibitor, such as, for example, orlistat.

In another embodiment of the invention, the compounds of the formula I are administered in combination with insulin.

In another embodiment, the compounds of the formula I are administered in combination with a sulfonylurea such as, for example, tolbutamide, glibenclamide, glipizide or glimepiride.

In another embodiment, the compounds of the formula I are administered in combination with a biguanide, such as, for example, metformin.

In another further embodiment, the compounds of the formula I are administered in combination with a meglitinide, such as, for example, repaglinide.

In another embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In another embodiment, the compounds of the formula I are administered in combination with an α-glucosidase inhibitor, such as, for example, miglitol or acarbose.

In another embodiment, the compounds of the formula I are administered in combination with an active ingredient which acts on the ATP-dependent potassium channel of the beta cells, such as, for example, totbutamide, glibenclamide, glipizide, glimepiride or repaglinide.

In another embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., in. Hormone and Metabolic Research (2001), 33(9), 554-558), NPY antagonists, e.g. naphthalene-1-sulfonic acid {4-[(4-aminoquinazolin-2-ylamino)methyl]cyclohexylmethyl}amide hydrochloride (CGP 71683A)), MC4 agonists (e.g. 1-amino-1,2,3,4-tetrahydronaphthalene-2-carboxylic acid[2-(3a-benzyl-2-methyl-3-oxo-2,3,3a ,4,6, 7-hexahydropyrazolo[4,3-c]pyridin-5-yl)-1-(4-chlorophenyl)-2oxoethyl]-amide; (WO 01/91752)), orexin antagonists (e.g. 1-(2-methylbenzoxazol-6-yl)-3-[1,5]naphthyrdidn-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trfluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In another embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment, the other active ingredient is dexamphetamine or amphetamine.

In another embodiment, the other active ingredient is fenfluramine or dexfenfluramine.

In another embodiment, the other active ingredient is sibutramine.

In another embodiment, the other active ingredient is mazindol or phentermine.

In another embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

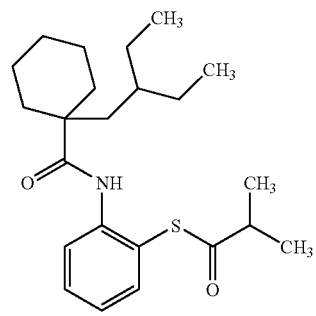

JTT-705

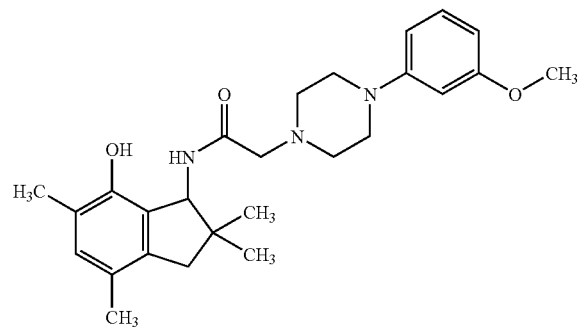

OPC-14117

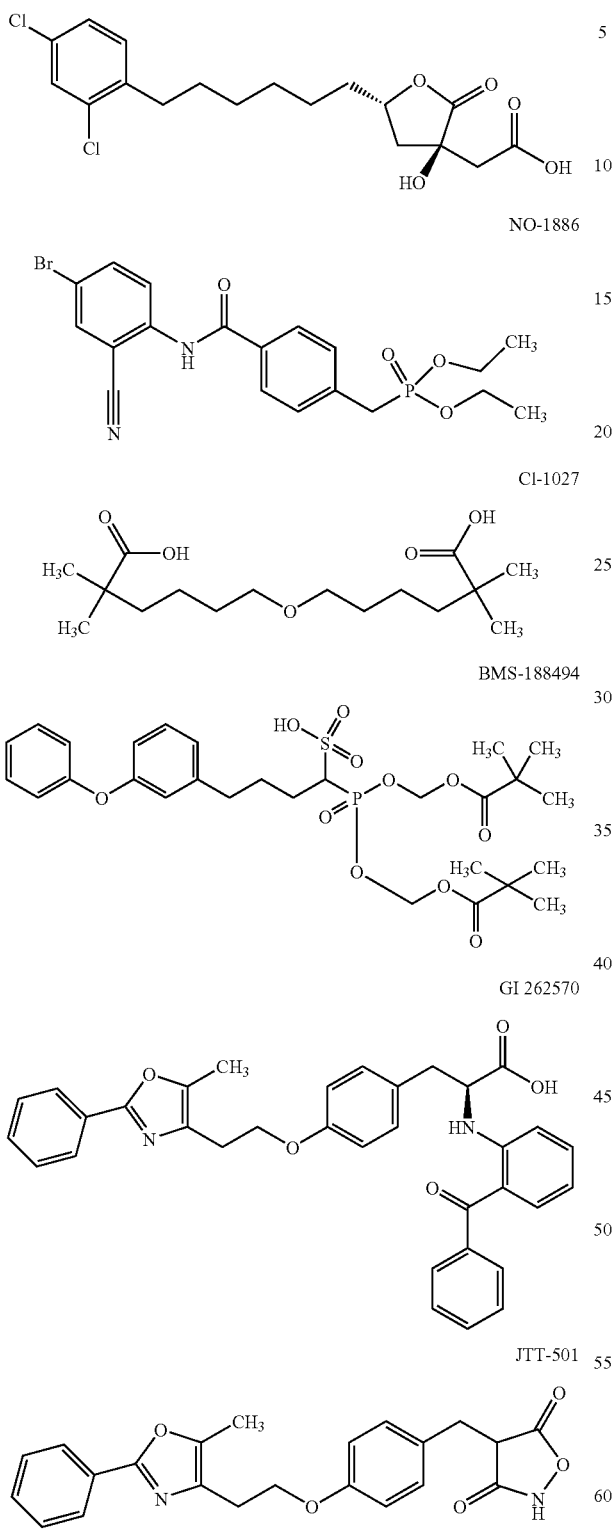

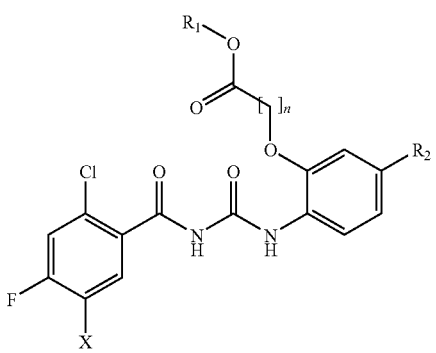

TABLE 1

Examples

| Example No. | X | R1 | R2 | n | m.p. [° C.] | MS |
|---|---|---|---|---|---|---|
| 1 | H | H | H | 1 | 180-181 | ok |
| 2 | H | H | COOH | 1 | 279-281 | ok |
| 3 | F | H | H | 1 | 179-180 | ok |
| 4 | F | Me | COOMe | 1 | 268 | ok |
| 5 | F | H | COOH | 1 | 294-297 | ok |
| 6 | F | H | H | 3 | 168 | ok |
| 7 | F | Me | H | 3 | 228 | ok |
| 8 | F | Me | COOMe | 3 | 209 | ok |
| 9 | F | H | COOH | 3 | 194 | ok |
| 10 | F | Me | COOH | 3 | 227 | ok |
| 11 | H | H | H | 4 | 197 | ok |
| 12 | H | H | COOH | 4 | 253-254 | ok |
| 13 | F | H | H | 4 | 164 | ok |
| 14 | F | H | COOH | 4 | 293-296 | ok |
| 15 | F | Me | COOH | 4 | 220 | ok |

\* The statement "MS is ok" means that a mass spectrum was recorded and the molecular peak (molecular mass + H⁺) was detected therein The compounds of the formula I are distinguished by beneficial effects on lipid and carbohydrate metabolism, they lower in particular the blood glucose level and they are suitable for the treatment of type 2 diabetes, of insulin resistance, of dyslipidemias and of the metabolic syndrome/syndrome X. The compounds are additionally suitable for the prophylaxis and treatment of arteriosclerotic manifestations. The compounds can be employed alone or in combination with other blood glucose-lowering active ingredients. The compounds of the formula I are also outstandingly suitable because of their pharmacological properties (see J. L. Treadway, P. Mendys, D. J. Hoover, Exp. Opin. Invest. Drugs 2001, 10(3), 439-454) as cardioprotective medicaments for the prophylaxis of infarction and the treatment of infarction, and for the treatment of angina pectoris, where they also preventively inhibit or greatly reduce the pathophysiological processes associated with the development of ischemia-induced damage, in particular in the triggering of ischemia-induced cardiac arrhythmias. The compounds can be employed alone or in combination with other cardioprotective or antiarrhythmic active ingredients. The compounds of the formula I are also because of their pharmacological properties of suitable for the treatment oncoses. It was possible to show in various investigations of this that there is a direct connection between the glycogen level and various parameters of tumor growth and tumor development (see M. Rousset, E. Dussauix, G. Chevalier, A. Zweibaum, J. Natl. Cancer Inst. 1980, 65(5), 885-889; K. Yano, S. Ohoshima, Y. Shimizu, T. Moriguchi, H. Katayama, Cancer Letters 1996, 110(1,2), 29-34; L. Skwarski, Z. Namiot, J. Stasiewicz, A. Kemona, M. Kralisz, J. Gorski, Cancer Letters 1998, 127(1,2), 123-128; S. Takahashi, A. Satomi, K. Yano, H. Kawase, T. Tanimizu, Y. Tuji, S.

The examples detailed below serve to illustrate the invention without, however, restricting it. The measured solidification or decomposition points have not been corrected and generally depend on the heating rate Murakami, R. Hirayama, J. Gastroenterology 1999, 34(4), 474-480). It is thus also possible to reduce tumor growth through manipulation of the amount of glucose released. The compounds of the formula I can for this purpose be employed where appropriate also in conjunction with other antitumor medicaments.

The efficacy of the compounds was tested as follows:

Analysis of Test Substances for their Inhibitory Potency on Glycogenolysis in Primary Cultures of Rat Hepatocytes Hepatocytes were isolated from the livers of fed rats (Sprague-Dawley or Wistar, bodyweight 220-240 g) by means of a standard 2-stage perfusion first with calcium-free buffer solution followed by perfusion with collagenase-containing solution to break up the tissue assembly (Seglen et al, 1979). The cells were incubated in an incubator with 90% humidity at 37° C. and an atmosphere with 5% $CO_2$ in air. The cultivation normally took place with Williams' medium E supplemented with 20 mM glucose, 0.1 mM fructose, 1 µM dexamethasone and 100 nM insulin. Glycogenolysis was induced by changing the culture medium to prewarmed carbogen-gassed Krebs-Henseleit bicarbonate Hepes (20 mM) buffer, pH 7.4, supplemented with 100 nM glucagon (time 0 min). The test substances were normally added at time 0 min as 100× stock solution in DMSO. The final DMSO concentration was not higher than 1% (v/v). The amount of glucose in the culture supernatant was determined after addition of glucagon in the presence and absence of test substance by removing small aliquots of the cell culture supernatant at times 0, 30, 60 and 90 min. The glucose concentration (mM) was determined by enzymatic methods in a biochemical analysis laboratory of Aventis Pharma Deutschland. The glucose production rate was found by linear regression of the glucose concentration at times 30, 60 and 90 min using the following formula:

Glucose production rate (mM/h)=mM glucose (90 min)−mM glucose (30 min).

The percent inhibition was calculated using the following formula:

$$\text{Percentage inhibition} = 100 \times \left[1 - \frac{\text{glucose production rate in the presence of test substance}}{\text{glucose production rate in the absence of test substance}}\right]$$

$IC_{50}$ values ($IC_{50}$: the concentration (µM) of test substance which brings about a reduction of 50% in the glucose production rate) was estimated by standard curve fitting methods using the percent inhibitions obtained at relevant concentrations of test substance.

TABLE 2

Biological activity

| Example No. | IC50 on hep. |
|---|---|
| 1 | 1.161 |
| 2 | 1.46 |
| 3 | 0.776 |
| 4 | 1.191 |
| 5 | 0.407 |
| 6 | 0.134 |
| 7 | 0.226 |
| 8 | 0.069 |
| 9 | <0.1 |
| 10 | 0.106 |
| 11 | 0.156 |
| 12 | 0.34 |
| 13 | 0.113 |
| 14 | 0.312 |
| 15 | 0.032 |

It is evident from the table that the compounds of the formula I inhibit glycogenolysis in rat hepatocytes and thus bring about a reduction in the blood glucose level.

Two compounds disclosed in WO 01/94300 were tested as comparison examples.

TABLE 2

Biological activity of comparison examples

| Structure | MW | $IC_{50}$ nm hep. [µM] |
|---|---|---|
| Example No. 105 from WO 01/94300 | 491.73 | 17.524 |
| Example No. 116 from WO 01/94300 | 457.28 | 13.522 |

It is evident from the table that the compounds of the formula I show an increased pharmacological effect. The effect of the compounds of the formula I is 11 to 548 fold higher than the effect of the comparison examples.

The preparation of some examples is described in detail below, and the other compounds of the formula I were obtained analogously:

EXPERIMENTAL PART

Example 1

2-[3-(2-Chloro-4-fluorobenzoyl)ureido]phenoxyacetic acid a) tert-Butyl 2-nitrophenoxyacetate 2.8 g (14.4 mmol) of tert-butyl bromoacetate and 2.6 g (7.9 mmol) of cesium carbonate are added to a solution of 1.0 g (7.2 mmol) of 2-nitrophenol in 20 ml of acetone. The suspension is heated to reflux for 48 hours. Then 50 ml of water are added, and the mixture is extracted twice with 50 ml of ethyl acetate each time. The combined organic phases are washed with water, dried over $Na_2SO_4$ and concentrated in a rotary evaporator. The product is employed without purification in the next step. Crude yield: 2.4 g b) tert-Butyl 2-aminophenoxyacetate 0.5 g of crude material from a) are dissolved in methanol and, after addition of 0.3 g of Raney Ni, hydrogenated with hydrogen at room temperature. The reaction is monitored by LC-MS.

After reduction is complete, the mixture is filtered with suction through Celite and washed with methanol. The filtrate is concentrated in a rotary evaporator, and the product is employed without purification in step d). Crude yield: 0.34 g c) 2-Chloro-4-fluorobenzoyl isocyanate 2-Chloro-4-fluorobenzamide was dissolved in dichloromethane and, after addition 1.5 eq. of oxalyl chloride, heated to reflux for 16 hours, The reaction mixture was concentrated under high vacuum and employed without further purification in stage d).

d) tert-Butyl 2-[3-(2-chloro-4-fluorobenzoyl)ureido]phenoxyacetate

A solution of 230 mg (1.2 mmol) of 2-chloro-4-fluorobenzoyl isocyanate in 5 ml of acetonitrile is added at room temperature to a solution of 129 mg (0.6 mmol) of tert-butyl 2-aminophenoxyacetate in 5 ml of dry acetonitrile under a protective gas atmosphere, The mixture is heated to reflux for 4 hours and cooled to room temperature. The solvent is distilled out in a rotary evaporator, and the resulting residue is employed without further purification in the next step. Crude yield: 0.33 g.

e) tert-Butyl 2-[3-(2-chloro-4-fluorobenzoyl)ureido]phenoxyacetate 0.33 g of crude material from stage d) are taken up in 10 ml of methylene chloride and, after addition of 10 ml of trifluoroacetic acid, stirred at room temperature for two hours. The solution is then concentrated after addition of 3 ml of toluene twice in a rotary evaporator, and the residue obtained in this way is purified in a preparative HPLC system (column: Waters Xterra™ MS $C_{18}$, 5 μm, 30×100 mm, mobile phases: A: $H_2O$+0.2% trifluoroacetic acid, B: acetonitrile, gradient: 2.5 minutes 90% A/10% B to 17.5 minutes 10% A/90% B). 88 mg (0.23 mmol) of the desired product are obtained.

Melting point: 180-181° C.

Example 3 was prepared in accordance with this method.

Example 2

3-Carboxymethoxy-4-[3-(2-chloro-4-fluorobenzoyl)ureido]benzoic acid a) Methyl 3-methoxycarbonylmethoxy-4-nitrobenzoate 0.77 g (5.1 mmol) of methyl bromoacetate and 0.91 g (2.8 mmol) of cesium carbonate are added to a solution of 0.50 g (2.5 mmol) of methyl 3-hydroxy-4-nitrobenzoate in 10 ml of acetone. The suspension is heated to reflux for 48 hours. Then 50 ml of water are added, and the mixture is extracted twice with 50 ml of ethyl acetate each time. The combined organic phases are washed with water, dried over $Na_2SO_4$ and concentrated in a rotary evaporator. Crude yield: 0.64 g b) 3-Carboxymethoxy-4-[3-(2-chloro-4-fluorobenzoyl)ureido]benzoic acid The crude product from step a) is converted in analogy to examples 1b) to 1d) into methyl 3-methoxycarbonylmethoxy-4-[3-(2-chloro-4-fluorobenzoyl)ureido]-benzoate, of which 50 mg (0.11 mmol) are dissolved in 5 ml of THF, and 1 ml of water is added. To this are added 27 mg (1.1 mmol) of LiOH, and the reaction is stirred at room temperature until the precursor has reacted completely. The reaction is monitored by LC-MS. After completion of the reaction, the mixture is acidified with dilute hydrochloric acid and extracted twice with 20 ml of ethyl acetate each time. The combined organic phases are dried over $Na_2SO_4$, filtered and concentrated in a rotary evaporator, and the residue obtained in this way is purified in a preparative HPLC system (column: Waters Xterra™ MS $C_{18}$, 5 μm, 30×100 mm, mobile phases: A: $H_2O$+0.2% trifluoroacetic acid, B: acetonitrile, gradient: 2.5 minutes 90% A/10% B to 17.5 minutes 10% A/90% B). 28 mg (0.068 mmol) of the desired product are obtained.

Melting point: 279-281° C.

Examples 4-9 and 11-14 were prepared in analogy to this method.

Example 10

4-[3-(2-Chloro-4,5-difluorobenzoyl)ureido]-3-(3-methoxycarbonylpropoxy)benzoic acid a) Benzyl 3-hydroxy-4-nitrobenzoate 2.0 g (11 mmol) of 3-hydroxy-4-nitrobenzoic acid are suspended in 25 ml of toluene, and 1.8 g (16 mmol) of benzyl alcohol and 0.2 g (1.1 mmol) of p-toluenesulfonic acid are added. The reaction is heated to reflux using a water trap until no further water separates out. After the reaction is complete, the solution is evaporated in a rotary evaporator and the crude product is purified by chromatography. Yield 1.6 g (5.9 mmol).

b) 4-[3-(2-Chloro-4,5-difluorobenzoyl)ureido]-3-(3-methoxycarbonylpropoxy)-benzoic acid The benzyl 3-hydroxy-4-nitrobenzoate from step a) was alkylated in analogy to method 2a) to form benzyl 3-(3-methoxycarbonylpropoxy)-4-nitrobenzoate. 450 mg (1.2 mmol) of the benzyl ester are dissolved in 20 ml of methanol and, after addition of 13 mg (0.1 mmol) of palladium on activated carbon (10%), hydrogenated at room temperature. The reaction is monitored by LC-MS. After the reduction is complete, the mixture is filtered with suction through Celite and washed with methanol. The filtrate is concentrated in a rotary evaporator, and the product is reacted without previous purification in analogy to method 1d) to give 4-[3-(2-chloro-4,5-difluorobenzoyl)ureido]-3-(3-methoxycarbonylpropoxy)-benzoic acid. The final purification takes place by preparative HPLC (column: Waters Xterra™ MS $C_{18}$, 5 μm, 30×100 mm, mobile phases: A: $H_2O$+0.2% trifluoroacetic acid, B: acetonitrile, gradient: 2.5 minutes 90% A/10% B to 17.5 minutes 10% A/90% B). Yield: 0.51 mg (0.11 mmol)

Melting point: 227° C.

Example 15 was prepared in analogy to this method.

The invention claimed is:

1. A compound of the formula I,

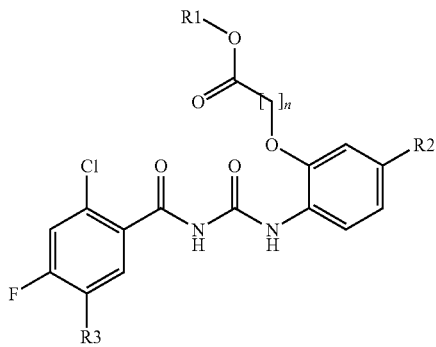

in which

R1 is H, $(C_1-C_6)$-alkyl or $(C_0-C_6)$-alkyl-phenyl wherein the phenyl ring is optionally mono- or disubstituted with F, Cl, Br, CN, OH, $(C_1-C_6)$-alkyl, O—$(C_1-C_6)$-alkyl, $CF_3$, $OCF_3$, COOH, COO$(C_1-C_6)$-alkyl or $CONH_2$;

R2 is H, $(C_1-C_6)$-alkyl, O—$(C_1-C_6)$-alkyl, CO—$(C_1-C_6)$-alkyl, COO—$(C1-C_6)$-alkyl or $(C_0-C_6)$-alkylene-COOH;

R3 is H, F, Cl, Br, OH, $CF_3$, $NO_2$, CN, $OCF_3$, O—$(C_1-C_6)$-alkyl or $(C1-C_6)$-alkyl; and n is 1, 2, 3, 4, 5, 6, 7 or 8;

and pharmaceutically acceptable salts thereof.

2. The compound of claim 1 wherein

R1 is H or $(C_1-C_6)$-alkyl;

R2 is H, $(C_1-C_6)$-alkyl, O—$(C_1-C_6)$-alkyl, CO—$(C_1-C_6)$-alkyl, COO—$(C_1-C_6)$ -alkyl or $(C_0-C_6)$-alkylene-COOH;

R3 is H, F, Cl, Br, OH, $CF_3$, $NO_2$, CN, $OCF_3$, O—$(C_1-C_6)$-alkyl or $(C_1-C_6)$-alkyl; and n is 1, 2, 3, 4, 5, 6, 7or 8;

and pharmaceutically acceptable salts thereof.

3. The compound of claim 2, wherein R1 is H or $(C_1-C_6)$-alkyl;

R2 is H, COO—$(C_1-C_6)$-alkyl or —COOH;

R3 is H or F; and n is 1, 2, 3 or 4;

and pharmaceutically acceptable salts thereof.

4. A pharmaceutical composition comprising a pharmaceutically acceptable carrier and one or more compounds of claim 1.

5. A pharmaceutical composition comprising a pharmaceutically acceptable carrier, one or more compounds of claim 1, and at least one other active ingredient.

6. The pharmaceutical composition of claim 5, wherein the other active ingredient comprises one or more antidiabetics, hypoglycemic active ingredients, antiobesics, anorexia, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbents, LDL receptor inducers, cholesterol absorption inhibitors (ezetimibe), ACAT inhibitors, antioxidants, lipoprotein lipase inhibitors, ATP-citrate lyase inhibitors, ACC inhibitors, squalene synthetase inhibitors, lipoprotein(a) antagonists, lipase inhibitors, insulins, sulfonylureas, biguanides, glitinides, thiazolidinediones, α-glucosidase inhibitors, glucagon-receptor antagonists, active ingredients which act on the ATP-dependent potassium channel of the beta cells, CART agonists, NPY agonists, GLP1 agonists, GIP agonists, MC4 agonists, MCH antagonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, LXR modulators, FXR modulators, uncoupling protein 2 or 3 modulators, leptin agonists, DA agonists (bromocriptine, Doprexin), lipase/amylase inhibitors, PPAR modulators, RXR modulators, TR-β agonists or amphetamines.

7. A method of reducing blood glucose comprising administering to a patient in need thereof a therapeutically effective amount of a compound of claim 1.

8. A process for producing a pharmaceutical composition comprising one or more of the compounds of claim 1 comprising mixing said compound of claim 1 with a pharmaceutically suitable carrier and converting this mixture into a form suitable for administration.

* * * * *

UNITED STATES PATENT AND TRADEMARK OFFICE
CERTIFICATE OF CORRECTION

PATENT NO. : 7,781,459 B2
APPLICATION NO. : 11/613433
DATED : August 24, 2010
INVENTOR(S) : Elisabeth DeFossa et al.

It is certified that error appears in the above-identified patent and that said Letters Patent is hereby corrected as shown below:

On the title page, in item (75), in column 1, 9th Inventor: "Buettleborn," should read as --Buettelborn, --.

On the title page, in item (30), in column 1, under "Foreign Application Priority Data", line 2, below "102 46 434" insert -- Sep. 22, 2003   (EP) .................... PCT/EP03/10501 --.

On page 2, in column 1, under "Other Publications", line 5, delete "Benzoylphnylureas," and insert -- Benzoylphenylureas, --, therefor.

In column 1, line 50, delete "($C_1$-$C_6$)alkyl," and insert -- ($C_1$-$C_6$)-alkyl, --, therefor.

In column 7, line 18, delete "totbutamide," and insert -- tolbutamide, --, therefor.

In column 7, line 32, delete "in." and insert -- in: --, therefor.

In column 7, line 40, delete "naphthyrdidn" and insert -- naphthyridin --, therefor.

In column 7, line 53, delete "trfluoroacetic" and insert -- trifluoroacetic --, therefor.

In column 9, line 67, after "rate" insert -- . --.

In column 10, line 58, delete "oncoses." and insert -- oncosis. --, therefor.

In column 10, line 62, delete "Dussauix," and insert -- Dussaulx, --, therefor.

In column 12, line 16, delete "IC50" and insert -- $IC_{50}$ --, therefor.

In column 13, line 49, delete "atmosphere," and insert -- atmosphere. --, therefor.

Signed and Sealed this
Twenty-eighth Day of June, 2011

David J. Kappos
*Director of the United States Patent and Trademark Office*

CERTIFICATE OF CORRECTION (continued)

U.S. Pat. No. 7,781,459 B2

In column 14, line 18-19, delete "methoxycarbonylrnethoxy0" and insert -- methoxycarbonylmethoxy --, therefor.

In column 15, line 29, in claim 1, delete "(C1-$C_6$)" and insert -- ($C_1$-$C_6$) --, therefor.

In column 15, line 29, in claim 1, delete "($C_o$-$C_6$)" and insert -- ($C_0$-$C_6$) --, therefor.

In column 15, line 32, in claim 1, delete "(C1-$C_6$)" and insert -- ($C_1$-$C_6$) --, therefor.

In column 15, line 35, in claim 2, delete "($C_1$-$C_6$-alkyl;" and insert -- ($C_1$-$C_6$)-alkyl; --, therefor.

In column 15, line 41, in claim 2, delete "7or 8;" and insert -- 7 or 8; --, therefor.